(12) United States Patent
Stenulson et al.

(10) Patent No.: US 9,572,601 B2
(45) Date of Patent: Feb. 21, 2017

(54) SPINAL CORRECTION ADJUSTMENT SYSTEMS AND METHODS

(71) Applicant: K2M, Inc., Leesburg, VA (US)

(72) Inventors: Matthew S. Stenulson, Hopkins, MN (US); Thomas J. Gisel, Chaska, MN (US); John F. Otte, Minneapolis, MN (US); Steven J. Seme, Savage, MN (US)

(73) Assignee: K2M, Inc., Leesburg, VA (US)

( * ) Notice: Subject to any disclaimer, the term of this patent is extended or adjusted under 35 U.S.C. 154(b) by 0 days.

(21) Appl. No.: 14/436,817

(22) PCT Filed: Oct. 17, 2013

(86) PCT No.: PCT/US2013/065488
§ 371 (c)(1),
(2) Date: Apr. 17, 2015

(87) PCT Pub. No.: WO2014/062942
PCT Pub. Date: Apr. 24, 2014

(65) Prior Publication Data
US 2016/0151096 A1     Jun. 2, 2016

Related U.S. Application Data

(60) Provisional application No. 61/715,005, filed on Oct. 17, 2012.

(51) Int. Cl.
*A61B 17/70* (2006.01)
(52) U.S. Cl.
CPC ....... *A61B 17/7052* (2013.01); *A61B 17/7001* (2013.01); *A61B 17/7014* (2013.01); *A61B 17/7041* (2013.01); *A61B 17/7053* (2013.01)

(58) Field of Classification Search
CPC ............ A61B 17/7001; A61B 17/7052; A61B 17/7041
See application file for complete search history.

(56) References Cited

U.S. PATENT DOCUMENTS

| | | | |
|---|---|---|---|
| 7,485,132 B1* | 2/2009 | McBride | A61B 17/7052 606/250 |
| 2002/0138077 A1* | 9/2002 | Ferree | A61B 17/7005 606/258 |

(Continued)

FOREIGN PATENT DOCUMENTS

FR     2900563 A1     11/2007

OTHER PUBLICATIONS

European Search Report dated May 4, 2016, issued in European Application No. 13846768.

(Continued)

*Primary Examiner* — Ellen C Hammond
*Assistant Examiner* — Stuart S Bray
(74) *Attorney, Agent, or Firm* — Carter, DeLuca, Farrell & Schmidt, LLP

(57) ABSTRACT

A system provides for lateral translational corrective force(s) and/or derotational corrective force(s) on a spinal column and includes highly adaptive hardware for connecting the system to the spinal column, where the hardware facilitates a more natural range of motion within pre-selected limits and application of such lateral translational and/or derotational corrective force(s). The upper and lower vertebral segments retain freedom of movement while an apical or restricted segment is restricted from relative vertebral movement. A central segment controls primary rod roll while the rod is free to change in pitch, yaw and roll at the upper (superior) and lower (inferior) segments.

22 Claims, 13 Drawing Sheets

(56) References Cited

U.S. PATENT DOCUMENTS

| | | | |
|---|---|---|---|
| 2002/0151978 A1* | 10/2002 | Zacouto | A61B 17/68 623/17.12 |
| 2004/0059330 A1* | 3/2004 | Biedermann | A61B 17/645 606/59 |
| 2005/0107789 A1* | 5/2005 | Sweeney | A61B 17/7052 606/86 A |
| 2006/0195088 A1* | 8/2006 | Sacher | A61B 17/7014 606/279 |
| 2006/0217718 A1* | 9/2006 | Chervitz | A61B 17/7064 606/247 |
| 2006/0247632 A1* | 11/2006 | Winslow | A61B 17/025 606/247 |
| 2007/0270803 A1* | 11/2007 | Giger | A61B 17/8076 606/60 |
| 2007/0270809 A1* | 11/2007 | Drewry | A61B 17/7052 606/279 |
| 2008/0109039 A1* | 5/2008 | Michielli | A61B 17/7049 606/251 |
| 2008/0255615 A1* | 10/2008 | Vittur | A61B 17/56 606/246 |
| 2009/0157120 A1* | 6/2009 | Marino | A61B 17/7049 606/278 |
| 2009/0210007 A1* | 8/2009 | Levy | A61B 17/7052 606/246 |
| 2010/0094302 A1* | 4/2010 | Pool | A61B 17/7004 606/90 |
| 2010/0174315 A1 | 7/2010 | Scodary et al. | |
| 2010/0217271 A1* | 8/2010 | Pool | A61B 17/7004 606/90 |
| 2010/0292734 A1* | 11/2010 | Bullard | A61B 17/7049 606/246 |
| 2011/0046675 A1* | 2/2011 | Barrus | A61B 17/7052 606/252 |
| 2011/0060367 A1* | 3/2011 | Stauber | A61B 17/7049 606/250 |
| 2011/0066188 A1* | 3/2011 | Seme | A61B 17/7041 606/264 |
| 2011/0172713 A1* | 7/2011 | Harper | A61B 17/7038 606/264 |
| 2012/0130436 A1* | 5/2012 | Haskins | A61B 17/7032 606/305 |
| 2013/0053888 A1* | 2/2013 | Torres | A61B 17/7052 606/252 |
| 2013/0090691 A1* | 4/2013 | Zhang | A61B 17/7001 606/264 |
| 2013/0123851 A1* | 5/2013 | Seme | A61B 17/70 606/250 |
| 2013/0268003 A1* | 10/2013 | Hwang | A61B 17/7052 606/251 |
| 2013/0338712 A1* | 12/2013 | Massenzio | A61B 17/7014 606/252 |
| 2014/0128919 A1* | 5/2014 | Okamoto | A61B 17/7052 606/252 |
| 2014/0236234 A1* | 8/2014 | Kroll | A61B 17/7014 606/264 |
| 2014/0277146 A1* | 9/2014 | Li | A61B 17/7052 606/252 |
| 2014/0316468 A1* | 10/2014 | Keiser | A61B 17/7052 606/252 |
| 2014/0336706 A1* | 11/2014 | Garamszegi | A61B 17/7052 606/252 |
| 2014/0358150 A1* | 12/2014 | Kaufman | A61B 17/025 606/90 |
| 2015/0080954 A1* | 3/2015 | Otte | A61B 17/7049 606/252 |
| 2015/0105834 A1* | 4/2015 | Bilger | A61B 17/68 606/86 R |
| 2015/0173818 A1* | 6/2015 | Baroud | A61B 17/8811 606/305 |
| 2015/0289906 A1* | 10/2015 | Murray | A61B 17/7001 606/263 |
| 2015/0305779 A1* | 10/2015 | Montavon | A61B 17/7001 606/257 |
| 2015/0374416 A1* | 12/2015 | Warren | A61B 17/58 606/247 |

OTHER PUBLICATIONS

Supplemental European Search Report dated Aug. 2, 2016, issued in European Application No. 13846768.

* cited by examiner

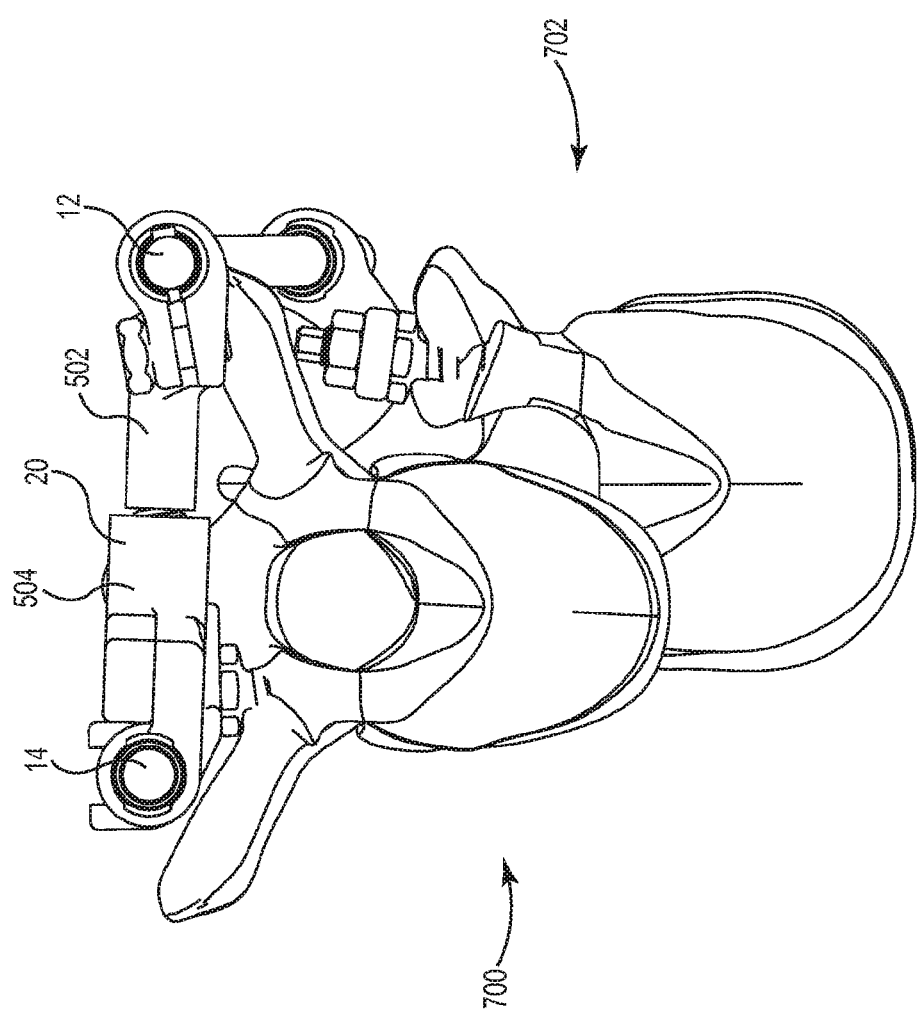

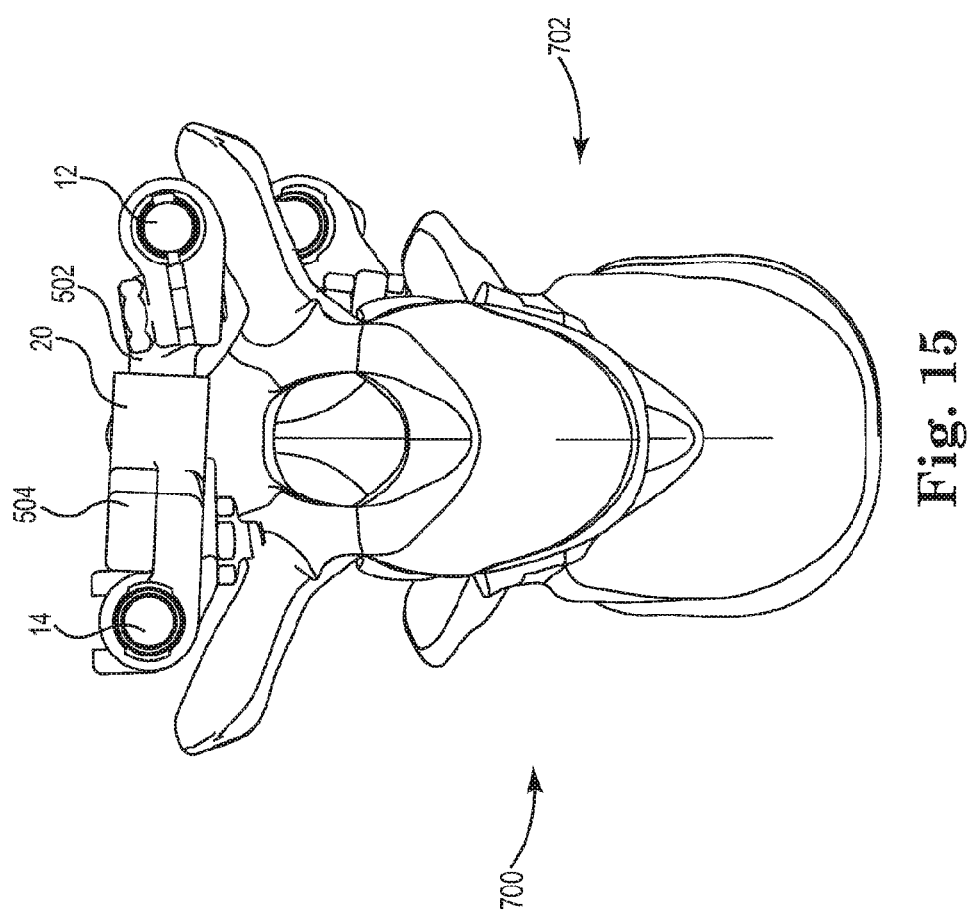

SPINAL CORRECTION ADJUSTMENT SYSTEMS AND METHODS

RELATED APPLICATIONS

This application is a national phase application of PCT Application No. PCT/US2013/065488, internationally filed Oct. 17, 2013, which claims the benefit of U.S. Provisional Application Ser. No. 61/715,005 filed Oct. 17, 2012 entitled SPINAL CORRECTION ADJUSTMENT SYSTEMS AND METHODS, both of which are incorporated by reference herein in their entirety.

INCORPORATION BY REFERENCE OF ADDITIONAL DISCLOSURES

Additional examples of system components and corrective methodology in accordance with various embodiments of the present invention are set forth in U.S. patent application Ser. No. 13/297,841, filed Nov. 16, 2011 and entitled "Spinal Correction and Secondary Stabilization"; U.S. App. Pub. 2010/0318129, filed Jun. 16, 2009 and entitled "Deformity Alignment System with Reactive Force Balancing"; U.S. App. Pub. 2010/0249837, filed Mar. 26, 2009 and entitled "Semi-Constrained Anchoring System"; U.S. App. Pub. 2011/0054536, filed Sep. 1, 2010 and entitled "Growth Directed Vertebral Fixation System with Distractible Connector(s) and Apical Control"; U.S. Pat. No. 7,658,753, issued Feb. 9, 2010 and entitled "Device and Method for Correcting a Spinal Deformity"; and U.S. App. Pub. 2009/0012565, filed on Jun. 5, 2008 and entitled "Medical Device and Method to Correct Deformity," the entire contents of each of which are hereby incorporated by reference for all purposes.

BACKGROUND

Many systems have been utilized to treat spinal deformities such as scoliosis, spondylolisthesis, and a variety of others. Primary surgical methods for correcting a spinal deformity utilize instrumentation to correct the deformity as much as possible, as well as implantable hardware systems to rigidly stabilize and maintain the correction. Presently, most of these implantable hardware systems rigidly fix the spinal column or allow limited growth and/or other movement of the spinal column, to help facilitate fusion after the column has been moved to a corrected position.

SUMMARY

Some aspects relate to methods of correcting a spinal deformity, including securing a first rod on a first side of a spine, securing an anchor on a second side of the spine, securing a lateral coupling between the rod and the anchor, translating and derotating the spine to correct the spinal deformity by adjusting an effective length of the lateral coupling, and securing a second rod on the second side of the spine to provide secondary stabilization to the spine.

Some embodiments relate to a coupler for an implantable spinal correction system. The coupler includes a first connector configured for securement to a first stabilizing member and a second connector configured for securement to at least one of a vertebral anchor or a second stabilizing member. A first slide member having a central bore is connected to the first connector and a second slide member having a central bore is connected to the second connector and telescopically received within the central bore of the first slide member. A drive member extends through the central bores of the first and second slide members and an actuator is coupled with the drive member such that rotation of the actuator causes rotation of the drive member resulting in relative, longitudinal movement between the first and second slide members.

Some embodiments relate to a system for spinal correction that includes a first stabilizing member for extending along a first side of a spine of a patient, a first stabilizing anchor for being secured at a superior spinal region on the first side of the spine and for receiving the first stabilizing member such that the first stabilizing member is able to change in pitch, yaw, and roll relative to the first stabilizing anchor while being substantially laterally constrained relative to the first stabilizing anchor and a second stabilizing anchor for being secured at an inferior spinal region on the first side of the spine and for receiving the first stabilizing member such that the first stabilizing member is able to change in pitch, yaw, and roll relative to the second stabilizing anchor while being substantially laterally constrained relative to the second stabilizing anchor. The system includes a second stabilizing member for extending along a second side of a spine of a patient and a lateral coupler for coupling the first and second stabilizing members. The lateral coupler includes a first connector configured for securement to the first stabilizing member that substantially prevents lateral movement of the first stabilizing member and prevents roll of the first stabilizing member with respect to the first connector and a second connector configured for securement to at least one of a vertebral anchor or the second stabilizing member, the second connector substantially preventing lateral movement of the vertebral anchor or the second stabilizing member. A first slide member is connected to the first connector and a second slide member is connected to the second connector and telescopically received within the first slide member. A first vertebral anchor for being secured to the second side of the spine includes a transverse arm including a terminal end extending away from the second side of the spine toward the first side of the spine. An adjustment mechanism for being secured to the first stabilizing anchor and exerting a correction force on the first vertebral anchor is configured to be secured to the terminal end of the transverse arm of the first vertebral anchor to define an effective length between the adjustment mechanism and the first vertebral anchor and is configured to shorten the effective length to exert the correction force.

Some embodiments relate to a method of correcting a spinal defect. A first stabilizing member is extended along a first side of a spine of a patient and a first stabilizing anchor is secured at a superior spinal region on the first side of the spine and receives the first stabilizing member with the first stabilizing anchor such that the first stabilizing member is able to change in pitch, yaw, and roll relative to the first stabilizing anchor while being substantially laterally constrained relative to the first stabilizing anchor. A second stabilizing anchor is secured at an inferior spinal region on the first side of the spine and receives the first stabilizing member with the second stabilizing anchor such that the first stabilizing member is able to change in pitch, yaw, and roll relative to the second stabilizing anchor while being substantially laterally constrained relative to the second stabilizing anchor. A second stabilizing member is extended along a second side of a spine of a patient and an apical region of the spine is derotated. The first and second stabilizing members are coupled such that the longitudinal axes of the first and second stabilizing members are substantially prevented from rotating relative to one another.

The second stabilizing member is laterally translated toward the first stabilizing member with the first and second stabilizing members substantially prevented from rotating relative to one another such that the apical region is laterally translated and the laterally translated and derotated position of the apical region of the spine is locked such that vertebra of the inferior and superior regions of the spine relative to the apical region of the spine retain the freedom of relative axial rotation and relative flexure in the anterior-posterior direction and the medial-lateral direction.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIGS. 12-15 are transverse views of a portion of a spine, shown in combination with the system of FIG. 1.

Figure 1:
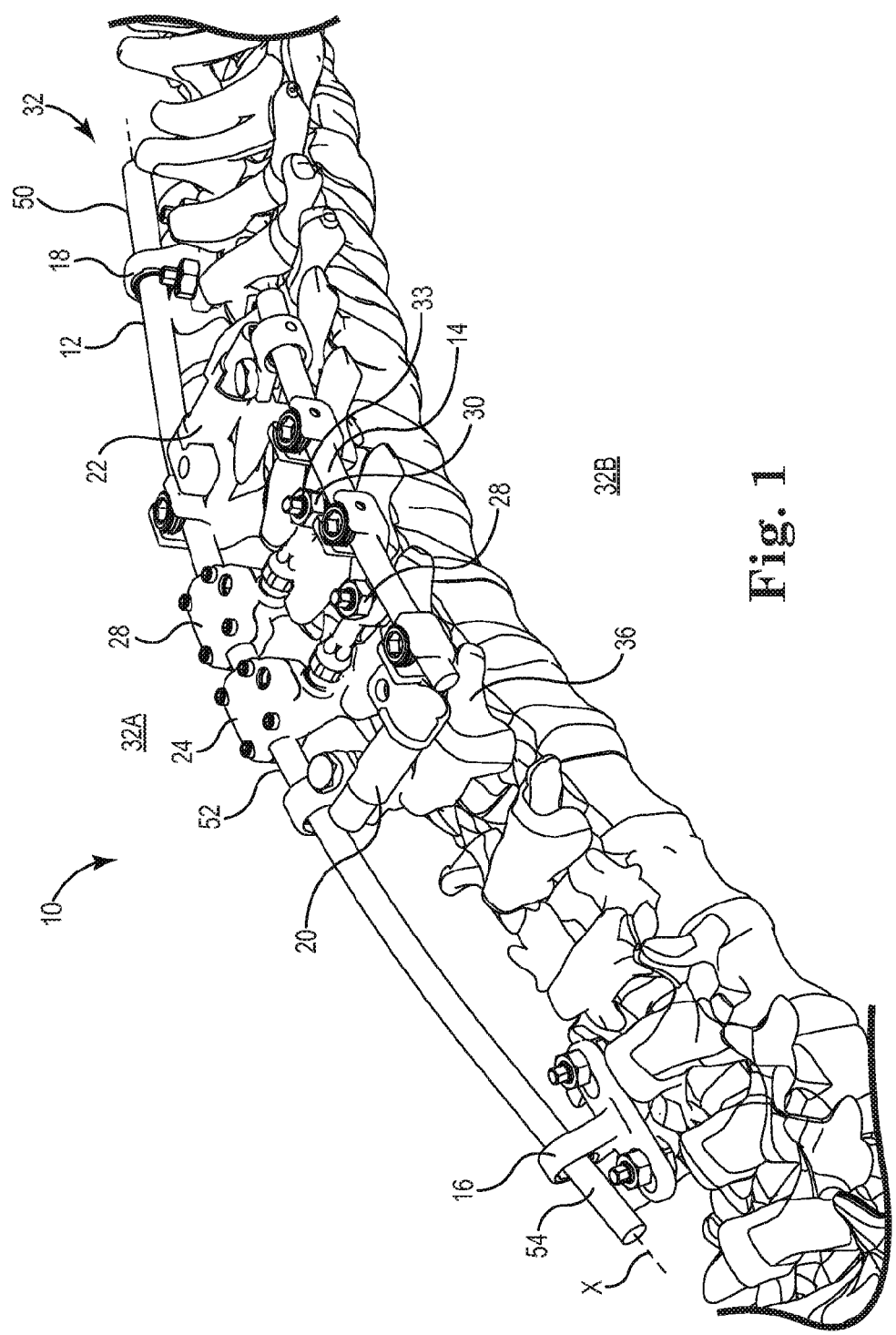
FIG. 1 is an isometric view of an implantable spinal correction and stabilization system, according to some embodiments.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Some embodiments relate to a system for correcting spinal deformities, as well as associated methods and devices. In general terms, the system provides for lateral translational corrective force(s) and/or derotational corrective force(s) on a spinal column. Some features of the system include highly adaptive hardware for connecting the system to the spinal column, where the hardware facilitates a more natural range of motion within pre-selected limits and application of such lateral translational and/or derotational corrective force(s). The upper and lower vertebral segments retain freedom of movement while an apical or restricted segment is restricted from relative vertebral movement. In various embodiments, a central segment controls primary rod roll while the rod is free to change in pitch, yaw and roll at the upper (superior) and lower (inferior) segments.

Some features of the system include implementation of a first, relatively, longer rod for initial correction and a second, shorter rod for secondary spinal stabilization. If desired, the secondary stabilization helps promote a fusion process. In some embodiments, the spine retains freedom of motion above and below the spinal segment corresponding to the shorter rod, with the first, relatively longer rod remaining implanted. In other embodiments, the first, relatively longer rod is trimmed and removed following correction of the spinal column and implementation of the second, shorter rod. A variety of additional features and advantages of the inventive systems are contemplated and provided by the instant disclosure.

Various planes and associated directions are referenced in the following description, including a sagittal plane defined by two axes, one drawn between a head (superior) and tail (inferior) of the body and one drawn between a back (posterior) and front (anterior) of the body; a coronal plane defined by two axes, one drawn between a center (medial) to side (lateral) of the body and one drawn between a head (superior) and tail (inferior) of the body; and a transverse plane defined by two axes, one drawn between a back and front of the body and one drawing between a center and side of the body.

The terms pitch, roll, and yaw are also used, where roll generally refers to angulation, or rotation, in a first plane through which a longitudinal axis of a body orthogonally passes (e.g., rotation about a longitudinal axis corresponding to the spinal column), pitch refers to angulation, or rotation, in a second plane orthogonal to the first plane, and yaw refers to angulation, or rotation, in a third plane orthogonal to the first and second planes. In some embodiments, pitch is angulation in the sagittal plane, yaw is angulation in the coronal plane, and roll is angulation in the transverse plane.

In various embodiments, changes in pitch, yaw, and/or roll occur concurrently or separately as desired. Moreover, as used herein, "lateral translation" is not limited to translation in the medial-lateral direction unless specified as such.

FIG. 1 shows a spinal correction and fusion system 10. The system 10 includes a first rod 12, a second rod 14 and a plurality of anchors and adjustors. In some embodiments, the system 10 includes a first stabilizing anchor 16 and a second stabilizing anchor 18 that locate the first rod 12 relative to a spine 32. As shown, the first rod 12 is disposed along a first side 32A of the spine 32 while the second rod 14 is disposed along a second side 32B of the spine 32. In some embodiments, the system 10 utilizes a variety of different anchors and adjustors, depending on the needs of the patient and the preferences of the physician.

As illustrated in FIG. 1, the system 10 includes a first lateral coupler 20 and a second lateral coupler 22. In some instances, the first lateral coupler 20 and the second lateral coupler 22 are configured to be adjustable in length. As shown, the system 10 includes a first adjustment mechanism 24 and a second adjustment mechanism 26. The first adjustment mechanism 24 and the second adjustment mechanism 26 are operably connected to a first anchor 28 and a second anchor 30, respectively. In some instances, the first adjustment mechanism 24 and the second adjustment mechanism 26 are connected via cables to the first anchor 28 and the second anchor 30, respectively, and are able to be manipulated to adjust an effective length of the cables extending therebetween. Some examples of suitable adjustment mechanisms are described in U.S. patent application Ser. No. 13/297,841; U.S. App. Pub. 2010/0318129; U.S. App. Pub. 2010/0249837; U.S. App. Pub. 2011/0054536; U.S. Pat. No. 7,658,753; and U.S. App. Pub. 2009/0012565, as previously incorporated by reference. Fasteners 33, such as bone screws, wires, adhesive means, or others, are used for securing various components of the system 10 to the spine 32.

The system 10 is optionally used to bring the spine 32 to a more natural curvature (e.g., using a single adjustment or multiple adjustments over time as desired). In other embodiments, an abnormal curvature in the spinal column 32 has been adjusted to a more natural curvature using other hardware, prior to or in conjunction with securing portions of the system 10 to the spinal column 37 in some embodiments, the system 10 is adapted to initially provide means for leveraged correction, with translation and derotation of the spine. If desired, the system 10 is adapted to provide means for stabilization of the spine following correction. Additionally, in various embodiments, the system 10 provides means for maintaining a correction to facilitate spine remodeling without vertebral fusion, or without permanent vertebral fusion.

Although the system 10 is shown with a select number of components, such as two stabilizing anchors 16, 18, two lateral couplers 20, 22, two adjustment mechanisms 24, 26 and two anchors 28, 30, more or fewer are implemented as appropriate. For example, in some embodiments a single adjuster, such as the first lateral coupler 20, is secured to one or more of a plurality of vertebrae 36 at an apex of a spinal deformation. As an example, a single lateral coupler such as the first lateral coupler 20 could be disposed between first and second adjustment mechanism 24, 26 and first and second anchors 28, 20.

In some embodiments, a single adjustment mechanism, such as the first adjustment mechanism 24, is secured to the first rod 12 with a corresponding anchor, such as the first anchor 28 secured to one or more of a plurality of vertebrae 36 at an apex of a spinal deformation. A variety of other configurations are also contemplated.

As shown in FIG. 1, the first rod 12, also described as an elongate member, is secured to the spinal column 32 at a pre-selected offset from a longitudinal axis of the spinal column 32. For example, the first rod 12 is optionally secured at an offset along a medial-lateral axis ML, or right-left axis, and anterior-posterior axis AP, or back-front axis. In some embodiments, the first rod 12 is secured on the left side of the spinal column 32 as shown. As subsequently described, the offset is selected to cause at least a relative lateral translation (e.g., central or medial movement) and/or derotational shift of selected vertebrae 36 of the spinal column 32 (relative anterior-posterior movement of selected vertebrae 36 can also be accomplished) such that the spinal column 32 exhibits a more natural position.

The first rod 12 is elongate and includes a superior portion 50, an intermediate portion 52, and an inferior portion 54. The first rod 12 is adapted, or otherwise structured, to extend along the spinal column 32. The first rod 12 is optionally contoured to complement a desired spinal curvature (e.g., generally following the curvature of a corrected or natural spine as shown in FIG. 20). In some embodiments, the first rod 12 is substantially rigid, defining a substantially round cross-section with a mean diameter of about 6 mm and being formed of a suitable biocompatible material, such as titanium alloy ASTM F136, or cobalt chromium alloy ASTM F1537 or any other suitable implantable material. If desired, the first rod 12 incorporates some flex, or springiness while substantially rigidly retaining its shape. The first rod 12 is optionally formed of a variety of materials, including stainless steel or suitable polymeric materials.

The first rod 12 has a longitudinal axis X—where the rod 12 is substantially straight, the longitudinal axis X is substantially straight and, where the rod 12 is substantially curved or angled, the longitudinal axis X is similarly curved or angled. The sections 50, 52, 54 of the first rod 12 are optionally continuously formed or are formed as separate, connected parts as desired. In still other embodiments, expandable rod designs are also contemplated.

As shown in FIG. 1, the second rod 14 is substantially shorter than the first rod 12. For example, the second rod 14 is optionally configured (e.g., having a corresponding length and/or longitudinal contour) to extend along an apical region of the spine 32. The second rod 14 is optionally formed of similar materials and with similar cross-section(s) to that of the first rod 12, as desired.

Figure 2:
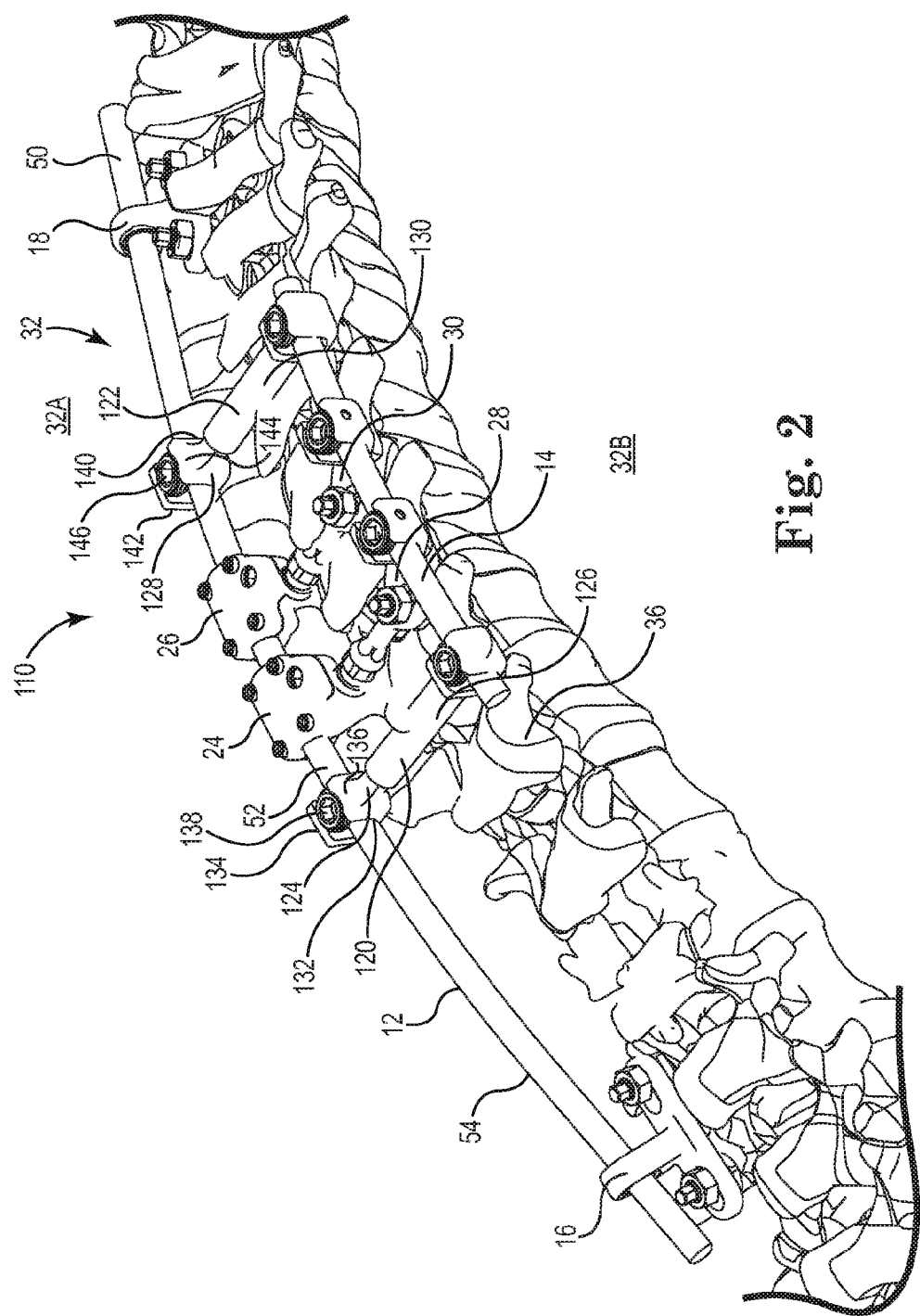
FIG. 2 is an isometric view of an implantable spinal correction and stabilization system, according to some embodiments.

FIG. 2 shows a spinal correction and stabilization system 110 in which the first lateral coupler 20 and the second lateral coupler 22 have been replaced with a first sliding coupler 120 and a second sliding coupler 122. Unlike the first and second lateral couplers 20, 22, the first and second sliding connectors 120, 122 do not include an internal mechanism that restricts changes in overall length. In some embodiments, the first and second sliding connectors 120, 122 include constraint mechanisms to fix the relative distance between the first rod 12 and the second rod 14.

As shown, the first and second sliding connectors 120, 122 are configured to self-adjust in length corresponding to the relative distance between the first rod 12 and the second rod 14 as the first and second adjustment mechanisms 24, 26 are manipulated to adjust an effective length of the cables extending between the first and second adjustment mechanisms 24, 26 and the corresponding first and second anchors 28, 30. As the second rod 14 moves toward the first rod 12, the first and second sliding connectors 120, 122 can shorten in length accordingly.

The first sliding coupler 120 includes a first connector 124 that is slidingly disposed within a second connector 126. Similarly, the second sliding coupler 122 includes a first connector 128 that is slidingly disposed within a second connector 130.

In this embodiment, the first connector 124 of the first sliding coupler 120 is configured to attach onto the first rod 12 such that the first rod 12 is prevented from moving relative to the first connector 124 of the first sliding coupler 120. The first rod 12 is optionally prevented from rotating or sliding relative to the first sliding coupler 120. As shown, the first connector 124 has a saddle shaped portion 132 including a first prong 134 and a second prong 136 spaced sufficiently apart from the first prong 134 to accommodate the first rod 12 therebetween. A retaining screw 138 can be threaded between the first prong 134 and the second prong 136 to secure the first connector 124 of the first sliding coupler 120 to the first rod 12.

Similarly, the first connector 128 of the second sliding coupler 122 is configured to attach onto the first rod 12 such that the first rod 12 is prevented from moving relative to the first connector 128 of the second sliding coupler 122. As shown, the first connector 128 has a saddle shaped head portion 140 including a first prong 142 and a second prong 144 spaced sufficiently apart from the first prong 142 to accommodate the first rod 12 therebetween. A retaining screw 146 is optionally threaded between the first prong 142 and the second prong 144 to secure the first connector 128 of the second sliding coupler 122 to the first rod 12.

Figure 3:
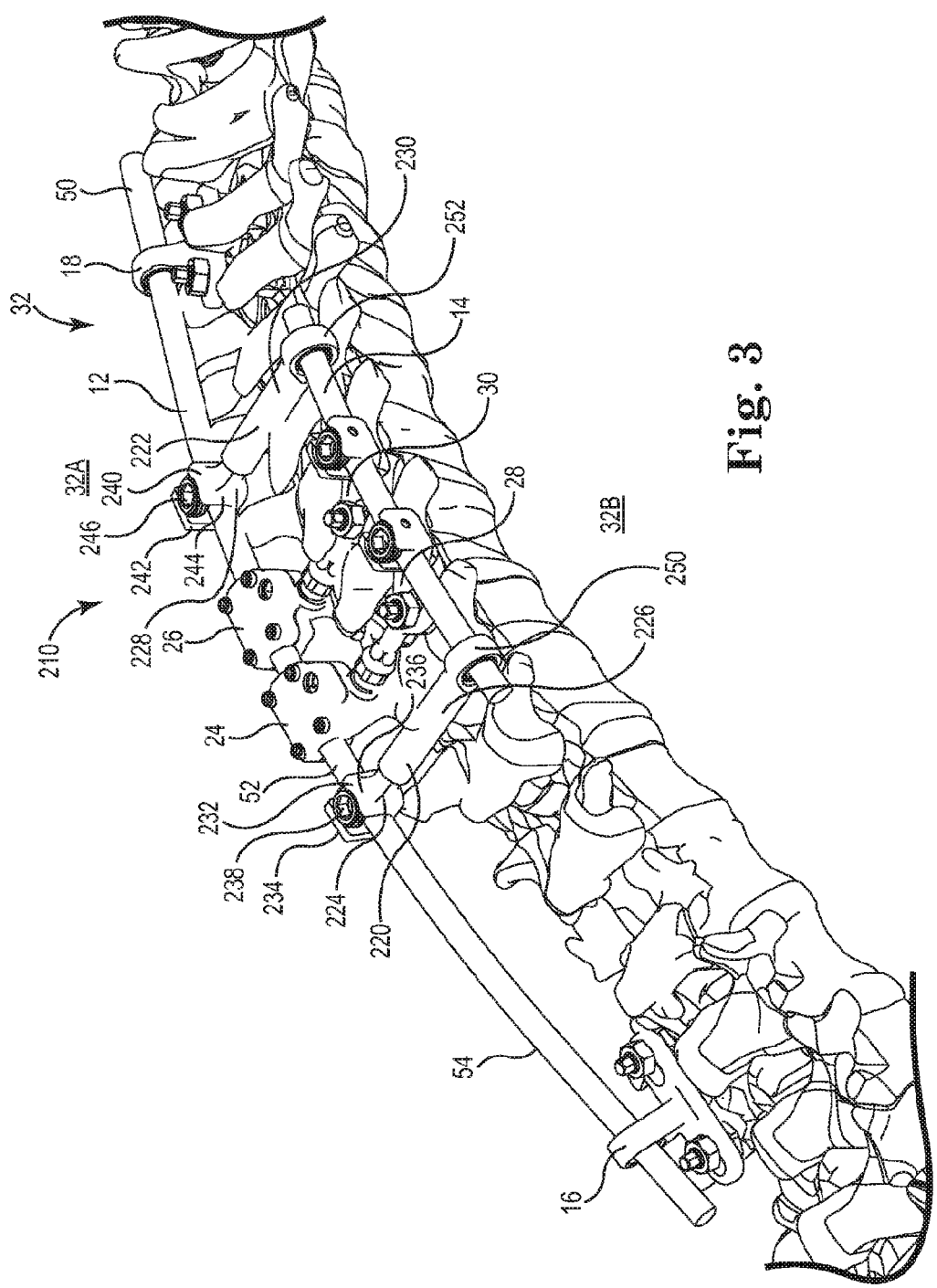
FIG. 3 is an isometric view of an implantable spinal correction and stabilization system, according to some embodiments.

FIG. 3 shows a spinal correction and stabilization system 210 in which the first lateral coupler 20 and the second lateral coupler 22 have been replaced with a first sliding coupler 220 and a second sliding coupler 222. Unlike the first and second sliding couplers 120, 122, the first and second sliding couplers 220, 222 are configured to facilitate securement to the first rod 12 while permitting sliding and rotational movement of the second rod 14. Optionally, the first and second sliding couplers 220, 222 are configured to facilitate securement to the second rod 14 while permitting sliding and rotational movement of the first rod 12.

The first and second sliding couplers 220, 222 are configured to self-adjust in length corresponding to the relative distance between the first rod 12 and the second rod 14 as the first and second adjustment mechanisms 24, 26 are manipulated to adjust an effective length of the cables extending between the first and second adjustment mechanisms 24, 26 and the corresponding first and second anchors 28, 30. The first sliding coupler 220 includes a first connector 224 that is slidingly disposed within a second connector 226. Similarly, the second sliding coupler 222 includes a first connector 228 that is slidingly disposed within a second connector 230.

In this embodiment, the first connector 224 of the first sliding coupler 220 is configured to attach onto the first rod 12 such that the first rod 12 is substantially prevented from moving relative to the first connector 224 of the first sliding coupler 220. As shown, the first connector 224 has a saddle shaped head portion 232 including a first prong 234 and a second prong 236 spaced sufficiently apart from the first prong 234 to accommodate the first rod 12 therebetween. A retaining screw 238 can be threaded between the first prong 234 and the second prong 236 to secure the first connector 224 of the first sliding coupler 220 to the first rod 12.

Similarly, the first portion 228 of the second sliding coupler 222 is configured to attach onto the first rod 12 such that the first rod 12 is prevented from moving relative to the first connector 228 of the second sliding coupler 222. As shown, the first connector 228 has a saddle shaped head portion 240 including a first prong 242 and a second prong 244 spaced sufficiently apart from the first prong 242 to accommodate the first rod 12 therebetween. A retaining screw 246 can be threaded between the first prong 242 and the second prong 244 to secure the first connector 228 of the second sliding coupler 222 to the first rod 12.

As shown, the second connector 226 of the first sliding coupler 220 includes a polyaxial joint 250 that is adapted to help permit the second rod 14 to move relative to the polyaxial joint 250 while substantially resisting transverse forces. In some instances, the second rod 14 is able to pitch and yaw with respect to the polyaxial joint 250. Optionally, the second portion 230 of the second sliding coupler 222 includes a polyaxial joint 252 that is configured to help permit the second rod 14 to move relative to the polyaxial joint 252 while substantially resisting transverse forces. In some instances, the second rod 14 is able to pitch and yaw with respect to the polyaxial joint 252. Optionally, the polyaxial joints 250, 252 help permit the second rod 14 to rotate and/or slide relative to the polyaxial joints 250, 252. This provides the clinical benefit of stabilizing while maintaining mobility and growth potential at a particular vertebral motion segment.

As shown, the first and second sliding couplers 220, 222 are configured such that they can substantially prevent movement of the first rod 12 while permitting movement of the second rod 14. In some embodiments, the first and second sliding couplers 220, 222 may be configured to substantially prevent movement of the second rod 14 while permitting movement of the first rod 12.

Figure 4:
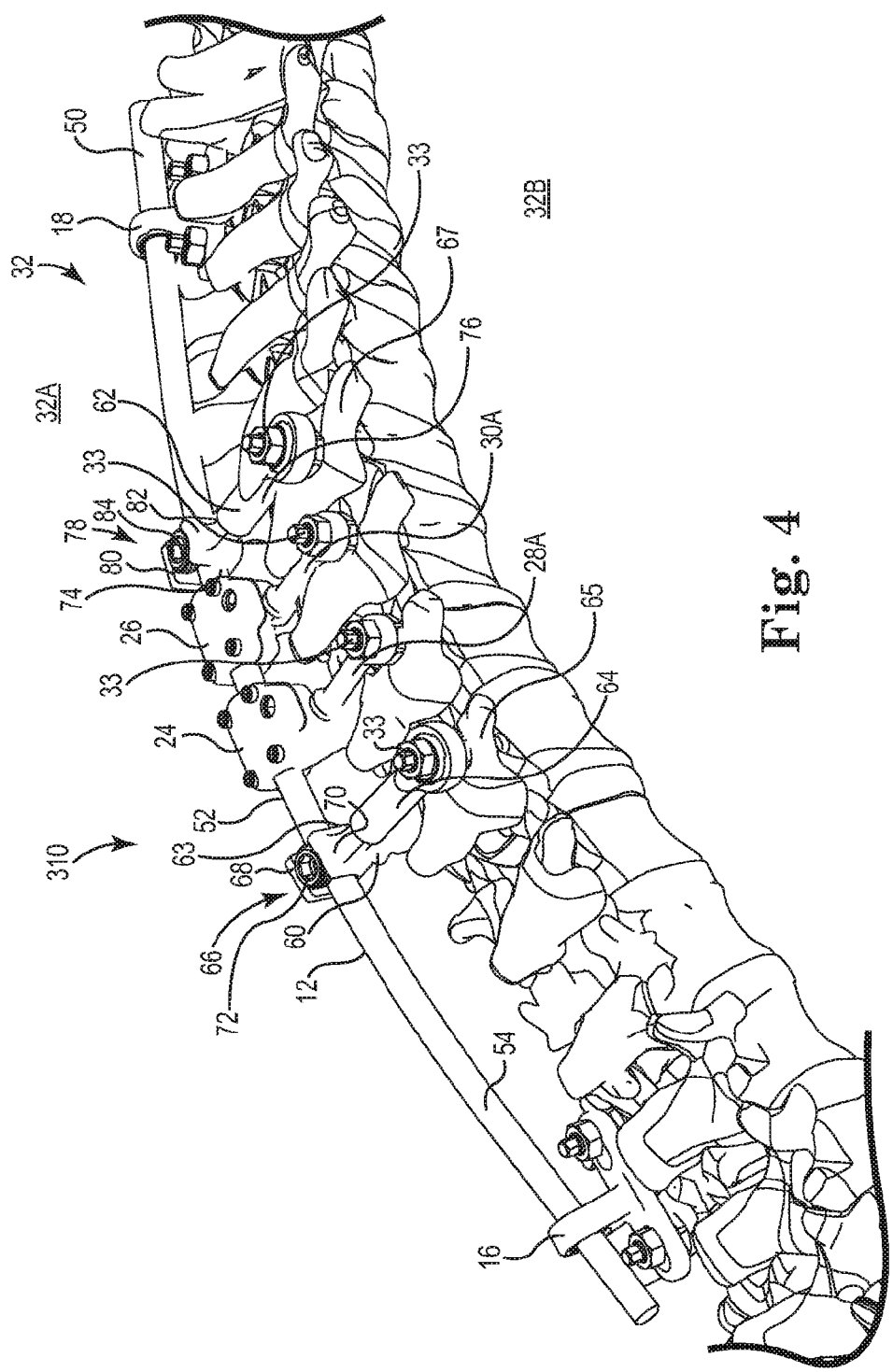
FIG. 4 is an isometric view of an implantable spinal correction and stabilization system, according to some embodiments.
Figure 6:
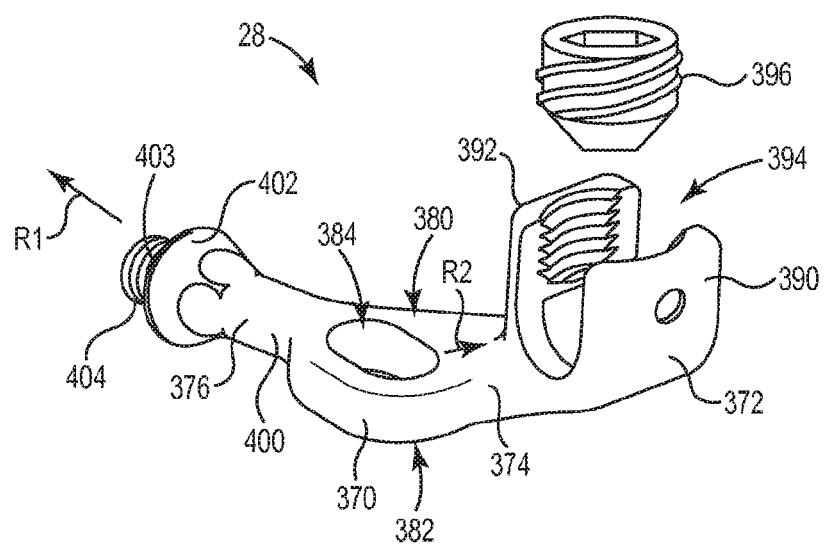
FIG. 6 is an isometric view of an anchor of the systems of FIGS. 1-4, according to some embodiments.

FIG. 4 shows a spinal correction and stabilization system 310 in which the second rod 14 has been excluded. The system 310 includes the first rod 12 extending between the first stabilizing anchor 16 and the second stabilizing anchor 18. First and second adjustment mechanisms 24, 26 are securable to the first rod 12. The first adjustment mechanism 24 and the second adjustment mechanism 26 are operably connected to a first anchor 28A and a second anchor 30A, respectively. The first anchor 28A and the second anchor 30A are similar to the first and second anchors 28, 30 shown in FIG. 1, but do not include a connection portion (such as connection portion 374 shown in FIG. 6) for accommodating the second rod 14. Optionally, the first adjustment mechanism 24 and the second adjustment mechanism 26 are connected via cables to the first anchor 28A and the second anchor 30A, respectively, and are able to be manipulated to adjust an effective length of the cables extending therebetween. Fasteners 33, such as bone screws, wires, adhesive means, or other, are used for securing various components of the system 10 to the spine 32.

The system 310 includes a first transverse coupler 60 and a second transverse coupler 62. The first transverse coupler 60 optionally includes a first connector 64 and a second connector 66 that is slidingly engaged with the first connector 64. The first transverse coupler 60 does not include an adjustment mechanism, but the first connector 64 is free to slide relative to the second connector 66 in order to accommodate movement between the first rod 12 and the spine 32 as the first and/or second adjustment mechanisms 24, 26 are actuated towards the rod 12. In other embodiments, the first transverse coupler 60 and the second transverse coupler 62 include an adjustment mechanism similar to the first lateral coupler 20 and the second lateral coupler 22.

The first connector 63 of the first transverse coupler 60 is configured to attach onto the first rod 12 such that the first rod 12 is prevented from moving relative to the first connector 63. The first rod 12 is optionally prevented from rotating or sliding relative to the first transverse coupler 60. As shown, the first connector 64 has a saddle shaped portion 66 including a first prong 68 and a second prong 70 spaced sufficiently apart from the first prong 68 to accommodate the first rod 12 therebetween. A retaining screw 72 can be threaded between the first prong 68 and the second prong 70 to secure the first connector 124 of the first transverse coupler 60 to the first rod 12.

Similarly, the second transverse coupler 62 includes a first connector 74 that is configured to attach onto the first rod 12 such that the first rod 12 is prevented from moving relative to the first connector 74 of the second transverse coupler 62. As shown, the first connector 74 has a saddle shaped head portion 78 including a first prong 80 and a second prong 82 spaced sufficiently apart from the first prong 78 to accommodate the first rod 12 therebetween. A retaining screw 84 is optionally threaded between the first prong 80 and the second prong 82 to secure the first connector 74 of the second transverse coupler 62 to the first rod 12.

The second connector 64 of the first transverse coupler 60 is configured for securement to the spine 32, such as to a vertebrae 65. The second connector 76 of the second transverse coupler 62 is configured for securement to the spine 32, such as to a vertebrae 67. The second connector 64 and the second connector 76 are adapted to be secured to the spine 32 using bone screws, wires or adhesive. Optionally, each of the second connector 64 and the second connector 76 are adapted to help permit the first and second transverse couplers 60, 62 to ungulate relative to the spine 32. The second connector 64 and the second connector 76 each form a polyaxial joint that substantially resists translational loads while allowing for angulation changes. In some instances, this will allow for continued realignment of the vertebral bodies when the first adjustment mechanism 24 and the second adjustment mechanism 26 are adjusted and allow for relative motion of the vertebral bodies with respect to the first rod 12 to assist with maintaining motion in the motion segment and preserving growth potential.

Figure 5:
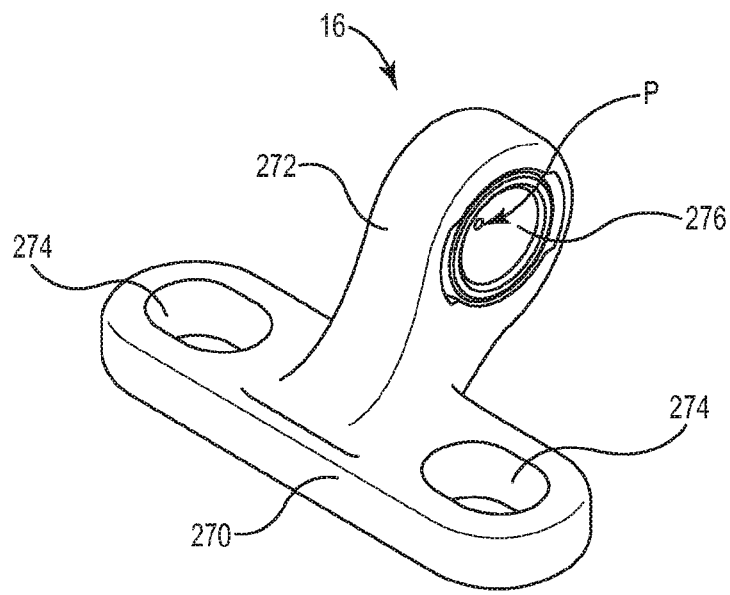
FIG. 5 is an isometric view of a stabilizing anchor, according to some embodiments.

FIG. 5 shows the first stabilizing anchor 16 in greater detail. In some embodiments, the second stabilizing anchor 18 is identical to the first stabilizing anchor 16, aside from relative location within the spinal correction and fusion system 10. Some examples of suitable stabilizing anchors are described in U.S. patent application Ser. No. 13/297,841; U.S. App. Pub. 2010/0318129; U.S. App. Pub. 2010/0249837; U.S. App. Pub. 2011/0054536; U.S. Pat. No. 7,658,753; and U.S. App. Pub. 2009/0012565, previously incorporated by reference. As shown in FIGS. 1-4, the first stabilizing anchor 16 is adapted, or otherwise structured, to be mounted, or fixed to one or more of the vertebrae 36 located at an inferior position, or other position, along the spine 32.

The first stabilizing anchor 16 is adapted to receive, and includes means for receiving, the first rod 12 such that the first rod 12 is secured laterally, against lateral translation relative to the first stabilizing anchor 16. In some embodiments, the first rod 12 is substantially prevented from translating in a direction substantially perpendicular to the longitudinal axis X at a pivot point P. In turn, the first rod 12 is able to slide axially, or translate axially, along the longitudinal axis X of the first rod 12, relative to the first stabilizing anchor 16 through the pivot point P. The rod 12 is also able to change in pitch and yaw about the pivot point P. In some embodiments, the first rod 12 is able to rotate about the longitudinal axis, depending on whether other components are tightened to the first rod 12.

The first stabilizing anchor 16 is optionally formed of biocompatible materials and includes a mounting portion 270 and a housing portion 272. The mounting portion 270 is adapted to secure the first stabilizing anchor 16 to one or more vertebrae 36. In other embodiments, the mounting portion 270 is secured to a single vertebra. As shown, the mounting portion 270, also described as a plate, is adapted to be secured at two or more points, for example spanning between two vertebrae 36 or across one vertebra 36.

In some embodiments, the mounting portion 270 includes a pedestal with first and second anchor locations, each of the anchor locations defining a surface suitable for mounting the first stabilizing anchor 16 to one or more vertebrae 36. The first and second anchor locations each optionally include through holes 274 for receiving one of the fasteners 33, such as a pedicle screw or similar device to secure the mounting portion 270 to one or more vertebrae 36. In some cases, the housing portion 272 includes a smooth bore 276 for accommodating the first rod 12.

The first and second anchors 28, 30 are optionally substantially similar, and thus various features of both the first and second anchors are described in association with the first anchor 28. The first anchor 28 is shown in greater detail in FIG. 6, according to some embodiments. As shown, the first anchor 28 includes a mounting portion 370, a head portion 372, a connection portion 374, and an arm portion 376. As shown, the mounting portion 370 has a top surface 380, a bottom surface 382, and a slot 384 for receiving one of the fasteners 33, such as a pedicle screw. The slot 384 is elongate and extends longitudinally in a first direction R1. In some embodiments, the arm portion 376 generally extends away from the mounting portion 370 for purpose of coupling to the first rod 12 and the head portion serves to couple the first transverse anchor 28 to the second rod 14. In other embodiments, the head portion is enclosed similar to the lateral coupler clamping portion 506.

The head portion 372 is substantially saddle shaped, including a first prong 390 and a second prong 392 defining a pocket 394 for receiving the second rod 14. As shown, the prongs 390, 392 are threaded for receiving a retaining screw 396 adapted to engage and secure the second rod 14 immobilized within the pocket 394.

The connection portion 374 extends in a second direction R2 that is offset from the first direction R1. The connection portion 374 extends between the mounting portion 370 and the head portion 372 at an angle of about 45 degrees, for example, relative to the first direction R1. In other embodiments, the connection portion 374 extends between the mounting portion and head portion 370, 372 at another angle, such as from about 30 to about 60 degrees, or at no angle (i.e., the portions 370, 372, 374 are generally in-line with one another).

The arm portion 376 includes a neck section 400 that is substantially elongate and cylindrical, a shoulder section 402 that is flared and defines an abutment face 403, and a terminal section 404 that is threaded. The arm portion 476 extends longitudinally in the first direction R1. The arm portion 476 is adapted to extend across a portion of one of the vertebrae 36 for example, from one side of the spinal column 32 to an opposite side of the spinal column 32. For example, the first anchor 28 is secured to one of the vertebrae 36 such that the arm portion 376 extends laterally across the vertebra 36.

Figure 7:
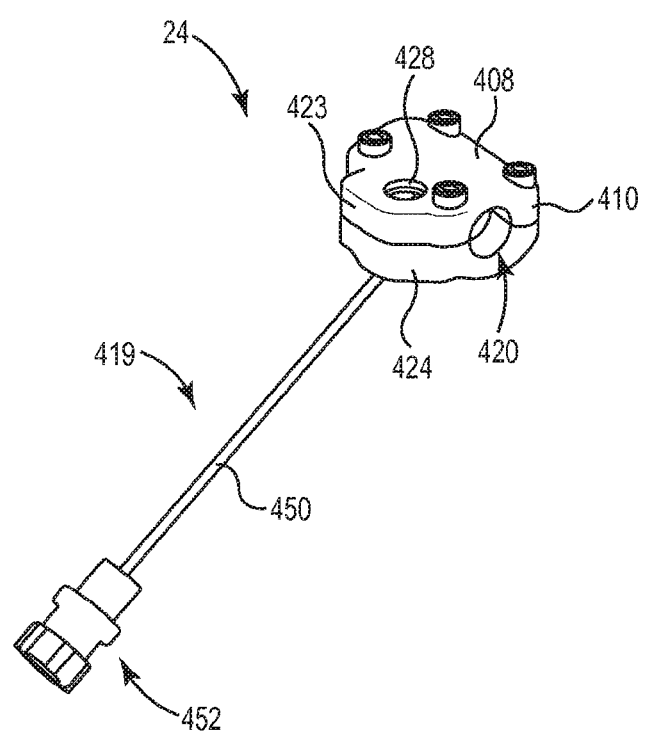
FIG. 7 is an isometric view of an actuation mechanism of the systems of FIGS. 1-4, according to some embodiments.

FIG. 7 shows the first adjustment mechanism 24 from an isometric view. The first adjustment mechanism 24 is adapted to adjust, and provides means for adjusting tension and/or a distance between the first rod 12 and the first anchor 28. The first and second adjustment mechanisms 24, 26 are optionally substantially similar. Thus, various features of both the first and second adjustment mechanisms 24, 26 are described in association with the first adjustment mechanism 24. The first and second adjustment mechanisms 24, 26 may be manipulated manually or by using a power source. The first and second adjustment mechanisms 24, 26 may be manipulated non-percutaneously.

As shown, the first adjustment mechanism 24 includes a tensioner 408 (internal to the housing 410). In some embodiments, the housing 410 defines a first side 423 and a second side 424 that together define a central lumen 420 for receiving the first rod 12 and incorporates a clamshell design (e.g., a first portion adjustably secured to a second portion) adapted to be tightened onto the first rod 12 (e.g., using one or more fasteners). Thus, the first adjustment mechanism 24 is optionally substantially fixed with respect to the first rod 12. Other designs, such as monolithic housing designs and others are contemplated. Moreover, in some embodiments, the first adjustment mechanism 24 is movable with respect to the first rod 12, for example being able to slide and/or rotate about the first rod 12.

The first adjustment mechanism 24 includes an elongate connector 419 that is adapted to secure to the first anchor 28.

The elongate connector 419 includes a flexible tether 450 and a connector head 452. In some embodiments, the flexible tether 450 is substantially flexible and able to be pivoted in a multiple directions and/or be spooled or wound, for example. Suitable flexible materials include wire and stranded cables, monofilament polymer materials, multifilament polymer materials, multifilament carbon or ceramic fibers, and others. In some embodiments, the flexible tether 450 is formed of cobalt chromium alloy or titanium alloy wire or cable, although a variety of materials are contemplated.

Some examples of suitable adjustment mechanisms are described in U.S. patent application Ser. No. 13/297,841; U.S. App. Pub. 2010/0318129; U.S. App. Pub. 2010/0249837; U.S. App. Pub. 2011/0054536; U.S. Pat. No. 7,658,753; and U.S. App. Pub. 2009/0012565, previously incorporated by reference.

Figure 8:
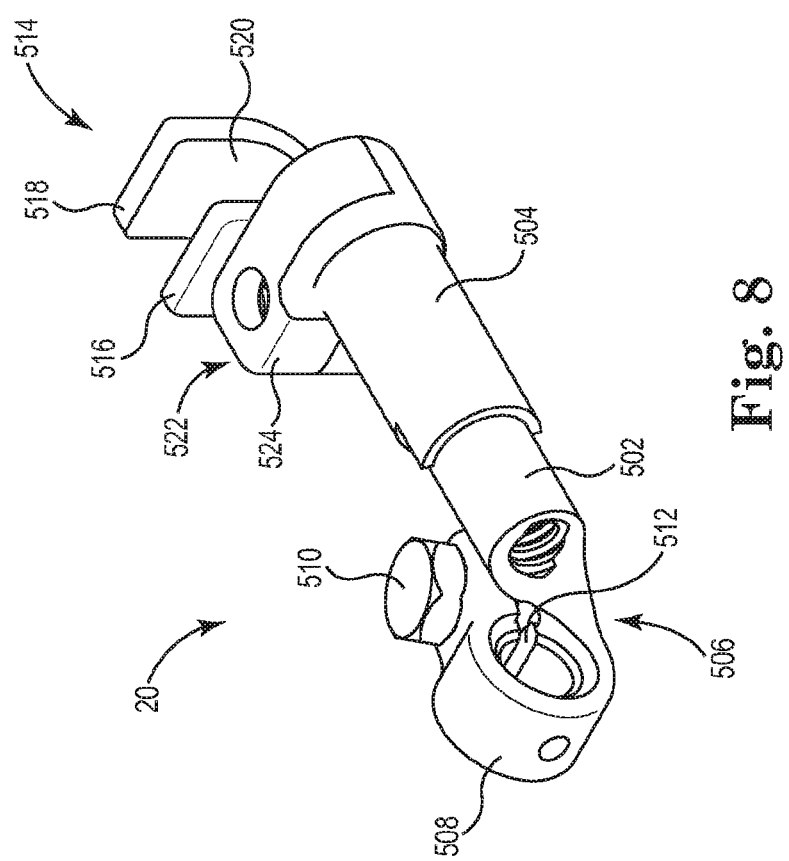
FIG. 8 is an isometric view of an adjustor of the system of FIG. 1, according to some embodiments.
Figure 9:
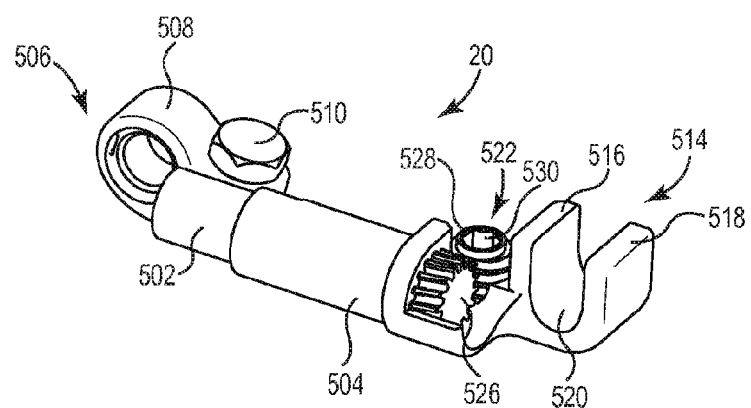
FIG. 9 is a partial cross-sectional view of the adjustor of FIG. 8, according to some embodiments.
Figure 10:
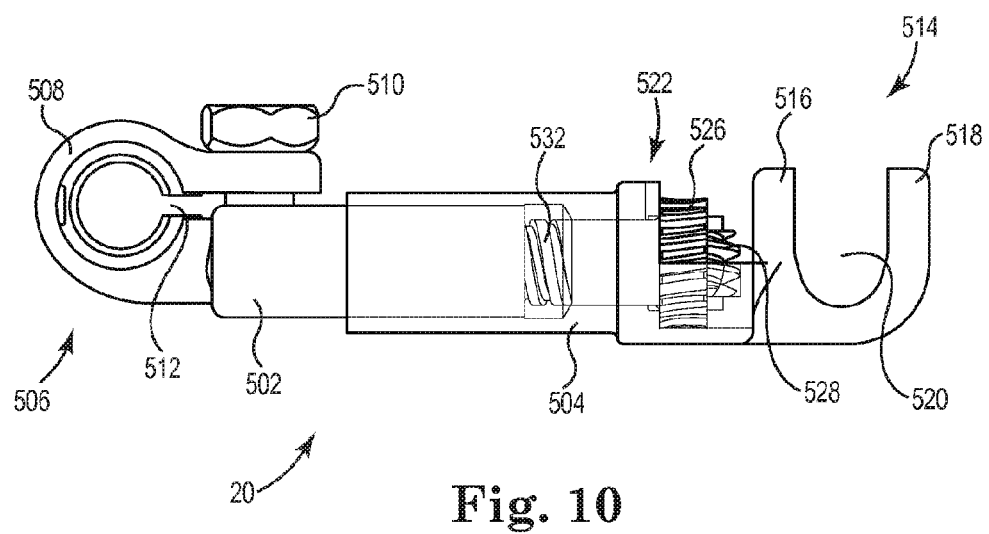
FIG. 10 is a partial cross-sectional view of the adjustor of FIG. 8, according to some embodiments.

FIG. 8 is an isometric view and FIGS. 9 and 10 are partial cutaway views of a first lateral coupler 20. In some embodiments, the first lateral coupler 20 and the second lateral coupler 22 are identical, apart from their relative locations on the spine 32. As shown, the first lateral coupler 20 includes a first connector 502 and a second connector 504 that is adapted to receive the first connector 502 in a telescoping fashion. The first connector 502 and the second connector 504 include a threaded interaction that helps permit the first connector 502 to translate relative to the second connector 504, thereby adjusting an overall length of the first lateral coupler 20.

As shown in FIG. 1, the first connector 502 includes a clamping portion 506 that is adapted for releasable securement to the first rod 12. The clamping portion 506 includes a curved clamp 508 and a fastener 510 that is threadedly engaged with the first portion 502 such that tightening the fastener 510 causes the curved clamp 508 to constrict to releasably lock the first rod 12 against changes in pitch, yaw or roll. In some instances, a gap 512 formed within the curved clamp 508 will narrow as the fastener 510 is tightened.

In some embodiments, as illustrated, the second connector 504 includes a head portion 514 that is substantially saddle shaped, including a first prong 516 and a second prong 518 defining a pocket 520 for receiving the second rod 14. The prongs 516, 518 are optionally threaded for receiving a retaining screw.

As noted, the first lateral coupler 20 is adapted to help permit the first connector 502 to translate relative to the second connector 504. As shown, the first lateral coupler 20 includes an offset portion 522 including a cover 524 and that is adapted to accommodate a gear connection between the first connector 502 and the second connector 504. As shown, the first connector 520 includes a circumferential gear 526 that interacts with an actuator or drive gear 528 in a worm-drive or crossed-spur gear configuration. The drive gear 528 is adapted to be rotated via a tool that fits into an aperture 530. The gear drive 528 may be driven manually or using a power tool. In some embodiments, the gear drive 528 may be manipulated non-percutaneously.

Rotating the drive gear 528 causes rotation of the circumferential gear 526. As the circumferential gear 526 rotates, a drive member such as a threaded relation 530 between the first connector 502 and the second connector 504 causes the first connector 502 to translate relative to the second connector 504. It will be appreciated that the first lateral coupler 20 may be shortened or lengthened, depending on which direction the drive gear 528 is rotated.

Figure 11:
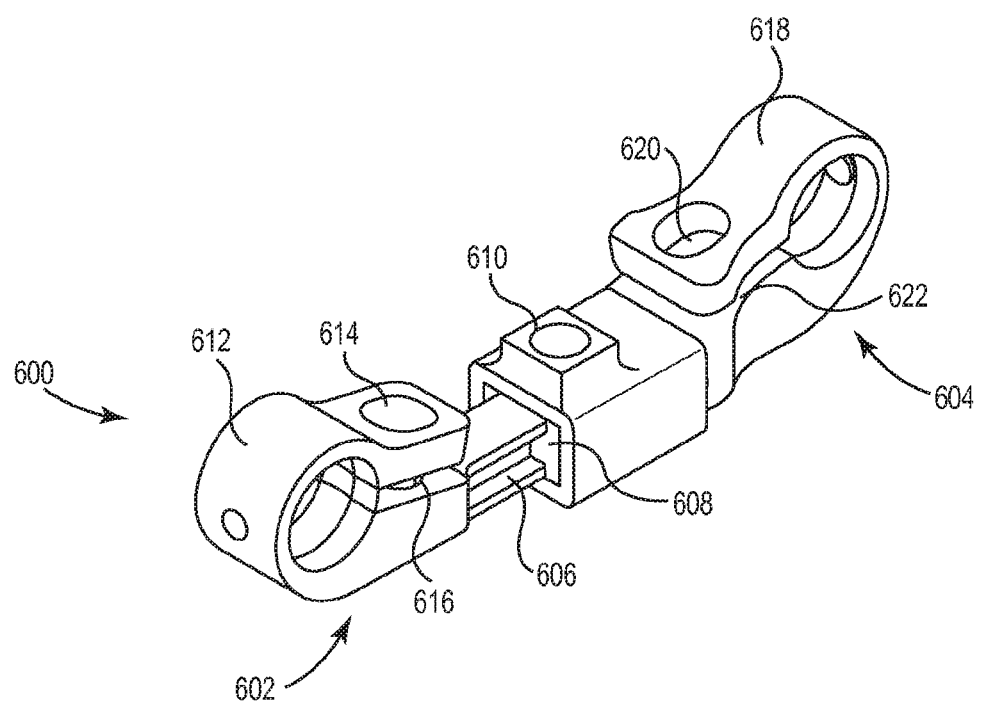
FIG. 11 is an isometric view of a sliding connector that may be used in the systems of FIGS. 2-3, according to some embodiments.

FIG. 11 is an isometric view of a sliding connector 600 that can be used with the spinal correction and stabilization system 10, 110 and 210. In some embodiments, the sliding connector 600 may be used in combination with or instead of one or more of the sliding connectors 120, 122, 220, 222 as desired. As shown, the sliding connector 600 includes a first connector 602 and a second connector 604 that is adapted to slidingly receive the first connector 602. In some instances, the first connector 602 includes an I-beam shaped portion 606 that is slidable into an insert 608. The insert 608 is optionally formed of a polymeric or ceramic material, for example, and serves as a guide rail for the I-beam shaped portion 606. In some embodiments, the second connector 604 includes a securement portion 610 for locking the first connector 602 relative to the second connector 604, such as by extending a fastener (not illustrated) through the securement portion 610.

As shown, the first connector 602 includes a clamping portion 612 that is adapted to receive either the first rod 12 or the second rod 14. The clamping portion 612 includes an aperture 614 adapted to accommodate a fastener that may threadedly engage a lower portion 616 in order to compress the clamping portion 612 onto either the first rod 12 or the second rod 14. Similarly, the second connector 604 includes a clamping portion 618 that is adapted to receive either the first rod 12 or the second rod 14. The clamping portion 618 includes an aperture 620 adapted to accommodate a fastener that may threadedly engage a lower portion 622 in order to compress the clamping portion 618 onto either the first rod 12 or the second rod 14.

In some embodiments, one or both of the first connector 602 and the second connector 604 have an end that helps permit movement of the rod 12, 14 therethrough, such as the polyaxial joints 250, 252 previously described with respect to FIG. 5. Optionally, the connectors described herein, such as sliding connectors 120, 122, 220, 222 have two ends that are adapted to help permit rod rotation and other movement. In some embodiments, one or more of the sliding connectors 120, 122, 220, 222 have two ends that are adapted to help prevent rod rotation and other movement. Optionally, one or more of the sliding connectors 120, 122, 220, 222 have a first end that is adapted to help permit rod movement and a second end that is adapted to help prevent rod movement.

Figure 12:
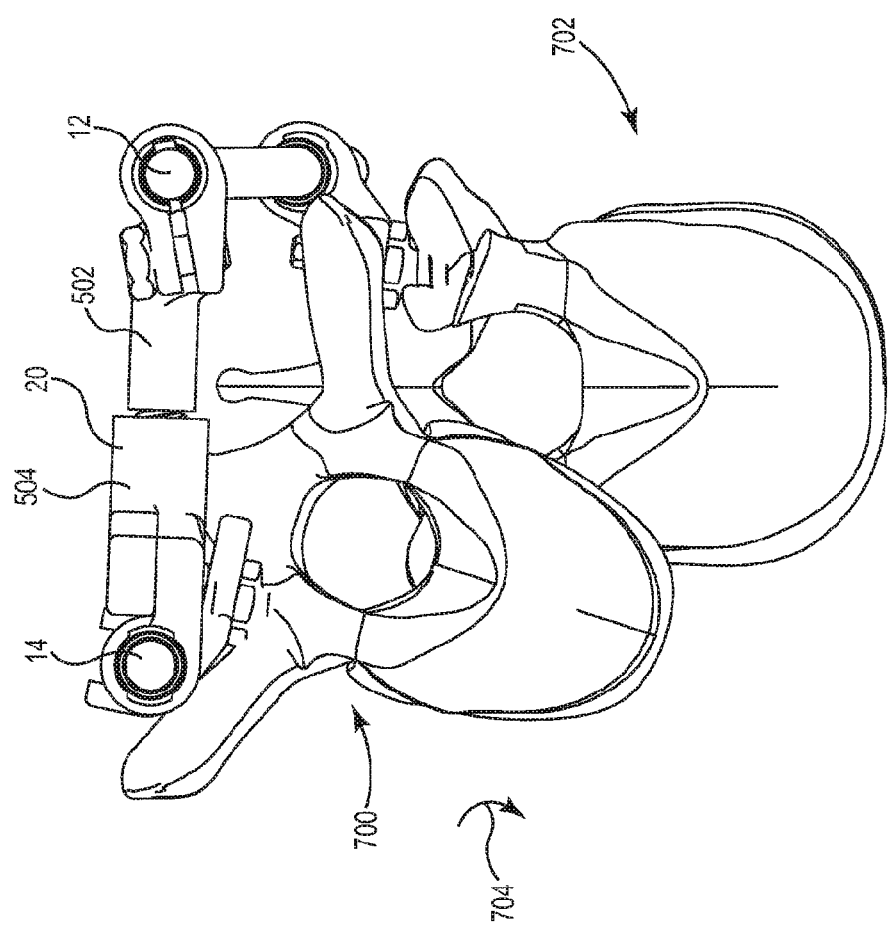

FIGS. 12-15 provide a transverse view of the system 10 relative to a first vertebrae 700 and a second vertebrae 702. In sequentially viewing the Figures, it can be seen that the vertebrae 700, 702 are first derotated [as shown by arrow 704], and then are locked against rotation by securing to the first and second rods 12, 14. FIG. 12 shows the spine 32 in an uncorrected state, or partially corrected state with the second rod 14 secured in the lateral coupler 20.

Figure 13:
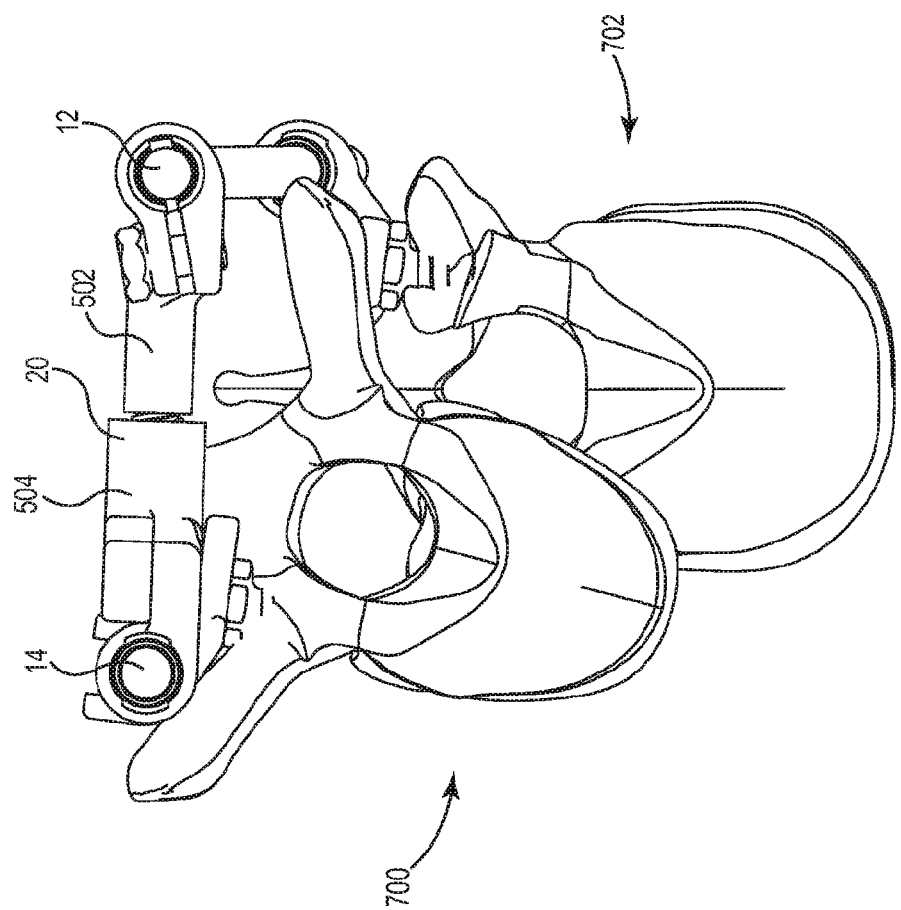

In order to assemble the second rod 14 into the system 10 (FIG. 1) or the system 110 (FIG. 2), a physician or other user can use a variety of tools and associated methods. With the second rod 14 assembled into the system 10 or 110, the user (not shown) optionally derotates the apical vertebrae of the spine 32, where FIG. 13 shows the apical vertebrae 700 in a partially derotated state and FIG. 14 shows the apical vertebrae 700 fully derotated. Derotation is optionally accomplished by grasping the second rod 14 with a tool (e.g., an appropriate surgical wrench or handled clamp) and rotating the second rod 14, the second rod 14 being free to rotate, or roll, within the lateral coupler 20.

Once fully derotated as shown in FIG. 14, the second rod 14 is locked against further changes in roll within the lateral coupler 20 and lateral adjustment commences to a laterally corrected state as shown in FIG. 15. In particular, the lateral couplers 20, 22 and/or adjustment mechanisms 24, 26 are operated in order to laterally translate the second rod 14 toward the first rod 12 to move the spine to a more laterally corrected configuration. For example, comparing FIG. 15 to FIG. 14, it can be seen that the first adjustor 20 has been significantly shortened, by viewing the position of the second portion 504 relative to the first portion 502.

Correction using the system 10 shown in FIG. 3 or 4 optionally proceeds similarly to that of the system 10 as shown in FIGS. 1 and 2. In some embodiments, however, systems 210 (FIG. 3) or 310 (FIG. 4) are fully locked by the physician or other user relative to the second rod 14 prior to partial or full derotation.

An illustrative but non-limiting example of correcting a spinal defect includes extending a first stabilizing member along a first side of a spine of a patient and securing a first stabilizing anchor at a superior spinal region on the first side of the spine and receiving the first stabilizing member with the first stabilizing anchor such that the first stabilizing member is able to change in pitch, yaw, and roll relative to the first stabilizing anchor while being substantially laterally constrained relative to the first stabilizing anchor. A second stabilizing anchor is secured at an inferior spinal region on the first side of the spine and the first stabilizing member is received within the second stabilizing anchor such that the first stabilizing member is able to change in pitch, yaw, and roll relative to the second stabilizing anchor while being substantially laterally constrained relative to the second stabilizing anchor.

A second stabilizing member is extended along a second side of a spine of a patient and an apical region of the spine is derotated. The first and second stabilizing members are coupled such that the longitudinal axes of the first and second stabilizing members are substantially prevented from rotating relative to one another. The second stabilizing member is laterally translated toward the first stabilizing member with the first and second stabilizing members substantially prevented from rotating relative to one another such that the apical region is laterally translated. The laterally translated and derotated position of the apical region of the spine is locked such that vertebra of the inferior and superior regions of the spine relative to the apical region of the spine retain the freedom of relative axial rotation and relative flexure in the anterior-posterior direction and the medial-lateral direction.

In some embodiments, if desired (e.g., once the spine 32 is stabilized), the first rod 12 is clipped, cut, broken, or otherwise portioned above the first stabilizing, anchor 16 and below the second stabilizing anchor 18. The superior and inferior portions of the first rod 12 are optionally removed from the first and second stabilizing anchors 16, 18 and the first and second stabilizing anchors 16, 18 are removed from the spine 32. As another alternative, the first rod 12 is not portioned and is left free to move in the stabilizing anchors 16, 18, for example. Moreover, if desired, the entire system 10 is optionally removed after a desired amount of stabilization of the spine has been achieved and/or after sufficient growth and remodeling of the spinal curvature has been achieved. For example, once a diseased area of the spine has sufficiently healed (e.g., after being realigned and stabilized) the stability provided by the system 10 may no longer be required.

Thus, according to various embodiments, the spinal column 32 (and thus, the person) is able to twist, bend side-to-side, and bend forward-and-backward in a more natural manner while corrective forces are being applied to the spinal column 32 and/or to achieve a desired correction of the spine 32. In some instances, removal of one or more portions of the system 10 (e.g., clipping and removing portions of the rod 12) facilitates this motion.

In some embodiments, by linking the convex and concave sides of the spine 32 together, stress on the spine 32 is distributed at the anchor-vertebral interfaces as well as stiffening the apical region of the spine, helping to stabilize the spine 32 in the maximum region of deformity. Thus, in addition to the connection between the apical region and the first rod 12, the lateral connection between the rods 12, 14 optionally helps resist vertebral rotation and lateral translation).

As previously indicated, in some embodiments, the spine 32 is optionally corrected, or tensioned toward the first rod 12 prior to securing the second rod 14 to the spine 40. In other embodiments, the corrective method includes securing the second rod 14 to the spine 32 (e.g., to partially or fully correct spinal curvature the apical region) and then tensioning the second rod 14 toward the first rod 12 in order to correct the spine 32 or portions thereof (e.g., a curvature of the spine 32 superior and/or inferior to the apical region).

Various modifications and additions can be made to the exemplary embodiments discussed without departing from the scope of the present invention. For example, while the embodiments described above refer to particular features, the scope of this invention also includes embodiments having different combinations of features and embodiments that do not include all of the above described features.

The following is claimed:

1. A coupler for an implantable spinal correction system, the coupler comprising:
    a first connector configured for securement to a first stabilizing member;
    a second connector configured for securement to at least one of a vertebral anchor or a second stabilizing member;
    a first slide member having a central bore and being connected to the first connector;
    a second slide member having a central bore and being connected to the second connector and telescopically received within the central bore of the first slide member;
    a drive member extending through the central bores of the first and second slide members; and
    an actuator coupled with the drive member defining an actuator rotation axis offset from a longitudinal axis of the drive member such that rotation of the actuator about the actuator rotation axis causes rotation of the drive member about its longitudinal axis resulting in relative, longitudinal movement between the first and second slide members along the longitudinal axis of the drive member.

2. The coupler of claim 1, wherein the drive member and the actuator are configured such that the drive member and the actuator automatically lock relative longitudinal movement between the first and second slide members when the actuator is not under an external rotational force.

3. The coupler of claim 1, wherein the drive member is a cylindrical member with a threaded exterior surface.

4. The coupler of claim 1, wherein the drive member has a first end portion and includes a gear at the first end portion and the actuator includes external threads mated with the gear of the drive member.

5. The coupler of claim 1, wherein the actuator is rotated manually.

6. The coupler of claim 1, wherein the actuator is rotated with a power source.

7. The coupler of claim 1, wherein the actuator is rotated non-percutaneously.

8. The coupler of claim 1, wherein the first connector has a saddle-shaped receptacle for receiving the first stabilizing member that substantially prevents lateral movement of the first stabilizing member and prevents roll of the first stabilizing member with respect to the first connector.

9. The coupler of claim 1, wherein the first connector is a polyaxial joint for receiving the first stabilizing member that substantially prevents lateral movement of the first stabilizing member and prevents roll of the first stabilizing member while allowing the first stabilizing member to change in pitch, yaw, and axial slide with respect to the first connector.

10. The coupler of claim 1, wherein the second connector is a polyaxial joint that substantially prevents lateral movement of the second stabilizing member while allowing the second stabilizing member to change in at least roll.

11. The coupler of claim 1, wherein the second connector is a polyaxial joint that substantially prevents lateral movement of the vertebral anchor while allowing the vertebral anchor to change in pitch, yaw, and roll with respect to the second connector.

12. The coupler of claim 1, wherein the second connector is configured for securement to the vertebral anchor and the second stabilizing member.

13. The coupler of claim 1, wherein the second connector has a saddle-shaped receptacle for receiving the second stabilizing member.

14. The coupler of claim 1, wherein the first slide member includes female threading at the central bore of the first slide member.

15. The coupler of claim 1, wherein the second slide member includes female threading at the central bore of the second slide member.

16. A system for spinal correction comprising:
a first stabilizing member for extending along a first side of a spine of a patient;
a first stabilizing anchor for being secured at a superior spinal region on the first side of the spine, the first stabilizing anchor receiving the first stabilizing member such that the first stabilizing member is able to change in pitch, yaw, and roll relative to the first stabilizing anchor while being substantially laterally constrained relative to the first stabilizing anchor;
a second stabilizing anchor for being secured at an inferior spinal region on the first side of the spine, the second stabilizing anchor receiving the first stabilizing member such that the first stabilizing member is able to change in pitch, yaw, and roll relative to the second stabilizing anchor while being substantially laterally constrained relative to the second stabilizing anchor;
a second stabilizing member for extending along a second side of a spine of a patient;
a lateral coupler coupling the first and second stabilizing members, the lateral coupler including:
a first connector secured to the first stabilizing member substantially preventing lateral movement of the first stabilizing member and preventing roll of the first stabilizing member with respect to the first connector;
a second connector secured to at least one of a vertebral anchor or the second stabilizing member, the second connector substantially preventing lateral movement of the at least one of the vertebral anchor or the second stabilizing member with respect to the second connector;
a first slide member connected to the first connector;
a second slide member connected to the second connector and telescopically received within the first slide member;
a drive member extending through the first and second slide members; and
an actuator coupled to the drive member and defining an actuator rotation axis offset from a longitudinal axis of the drive member such that rotation of the actuator about the actuator rotation axis causes rotation of the drive member about its longitudinal axis resulting in relative, longitudinal movement between the first and second slide members;
a first vertebral anchor securable to the second side of the spine and including a transverse arm including a terminal end extending away from the second side of the spine toward the first side of the spine; and
an adjustment mechanism securable to the first stabilizing member, the adjustment mechanism secured to the terminal end of the transverse arm of the first vertebral anchor and defining an effective length between the adjustment mechanism and the first vertebral anchor, the adjustment mechanism configured to shorten the effective length to exert a correction force on the first vertebral anchor.

17. The system of claim 16, wherein the first vertebral anchor includes a receptacle for receiving the second stabilizing member, the receptacle being configured to be selectively locked to the second stabilizing member such that the second stabilizing member is substantially prevented from changing in pitch, yaw, and roll relative to the receptacle and is laterally constrained by the receptacle.

18. The system of claim 16, wherein the lateral coupler is configured to allow roll of the second stabilizing member.

19. The system of claim 16, wherein the first vertebral anchor includes a fastener portion configured to provide a polyaxial connection to a vertebral fastener.

20. The system of claim 16, wherein the drive member and the actuator are configured such that the drive member and the actuator automatically lock relative longitudinal movement between the first and second slide members when the actuator is not under an external rotational force.

21. The system of claim 16, wherein the first slide member is substantially prevented from axial rotation relative to the second slide member.

22. A method of correcting a spinal defect, comprising:
extending a first stabilizing member along a first side of a spine of a patient;
securing a first stabilizing anchor at a superior spinal region on the first side of the spine and receiving the first stabilizing member with the first stabilizing anchor such that the first stabilizing member is able to change in pitch, yaw, and roll relative to the first stabilizing anchor while being substantially laterally constrained relative to the first stabilizing anchor;
securing a second stabilizing anchor at an inferior spinal region on the first side of the spine and receiving the first stabilizing member with the second stabilizing anchor such that the first stabilizing member is able to change in pitch, yaw, and roll relative to the second stabilizing anchor while being substantially laterally constrained relative to the second stabilizing anchor;
extending a second stabilizing member along a second side of a spine of a patient;
derotating an apical region of the spine;
coupling the first and second stabilizing members with a coupler such that the longitudinal axes of the first and second stabilizing members are substantially prevented from rotating relative to one another;

rotating an actuator of the coupler about an actuator axis offset from a longitudinal axis of the coupler to laterally translate the second stabilizing member toward the first stabilizing member with the first and second stabilizing members substantially prevented from rotating relative to one another such that the apical region is laterally translated; and locking the laterally translated and derotated position of the apical region of the spine with the coupler such that vertebrae of the inferior and superior regions of the spine relative to the apical region of the spine retain the freedom of relative axial rotation and relative flexure in the anterior-posterior direction and the medial-lateral direction.

* * * * *